US005480443A

United States Patent [19]
Elias

[11] Patent Number: 5,480,443
[45] Date of Patent: Jan. 2, 1996

[54] ARTIFICAL IMPLANT COMPONENT AND METHOD FOR SECURING SAME

[76] Inventor: Sarmed G. Elias, 2740 W. Foster, Ste. 301, Chicago, Ill. 60625

[21] Appl. No.: 204,815

[22] Filed: Mar. 2, 1994

Related U.S. Application Data

[63] Continuation of Ser. No. 828,638, Jan. 31, 1992, abandoned.

[51] Int. Cl.$^6$ ................................................ A61F 2/38
[52] U.S. Cl. ............................................. 623/18; 623/20
[58] Field of Search .................................. 623/16, 18, 20, 623/22, 23; 606/60, 91, 92, 93, 94, 95

[56] References Cited

U.S. PATENT DOCUMENTS

| | | | |
|---|---|---|---|
| 3,964,106 | 6/1976 | Hutter, Jr. et al. | 623/20 |
| 4,094,017 | 6/1978 | Matthews et al. | 623/20 |
| 4,302,855 | 12/1981 | Swanson | 623/16 |
| 4,563,778 | 1/1986 | Roche et al. | 606/92 X |
| 4,964,867 | 10/1990 | Boger | 623/20 |
| 5,019,104 | 5/1991 | Whiteside et al. | 623/20 |
| 5,197,986 | 3/1993 | Mikhail | 623/20 |

FOREIGN PATENT DOCUMENTS

| | | | |
|---|---|---|---|
| 437173 | 7/1991 | European Pat. Off. | 623/20 |
| 0307654 | 3/1989 | Germany | 623/20 |
| WO91/15168 | 10/1991 | WIPO | 623/20 |

OTHER PUBLICATIONS

Advertising material regarding the Freeman–Samulson Knee (Exhibit A of the Affidavit of Sarmed George Elias).
Advertising material regarding the Smith & Nephew Richards Knee (Exhibit B of the Affidavit of Sarmed George Elias).
Advertising material regarding the AGC Knee System marketed by Biomet (Exhibit C of the Affidavit of Sarmed George Elias).
Advertising material regarding the OMNIFIT Knee System marketed by Osteonics (Exhibit D of the Affidavit of Sarmed George Elias).
Advertising material regarding the Miller–Galante Knee (Exhibit E of the Affidavit of Sarmed George Elias).
Advertising material regarding the Insall/Burstein Knee System marketed by Zimmer (Exhibit F of the affidavit of Sarmed George Elias).
Advertising material regrding the PCA Modular Knee System (Exhibit G of the Affidavit of Sarmed George Elias).
Advertising material regarding the Kinemax Plus Knee System manufactured by Howmedica (Exhibit H of the Affidavit of Sarmed George Elias).
Advetising material regarding the PFC Knee System marketed by Johnson & Johnson (Exhibit I of the Affidavit of Sarmed George Elias).
Advertising material regarding the Genesis Knee System marketed by Smith & Nephew Richards (Exhibit J of the Affidavit of Sarmed George Elias).
Advertising material regarding the AMK System being manufactured by DePuy (Exhibit K of the Affidavit of Sarmed George Elias).

*Primary Examiner*—Mary Beth O. Jones
*Attorney, Agent, or Firm*—Harness, Dickey & Pierce

[57] ABSTRACT

An artificial patella component operable to articulate with the femoral component of a knee prosthesis as well as being securely fixed to the natural patella. The artificial patella component including a dome-shaped portion having a spherical articular surface which is able to articulate with the femoral component of a knee joint prosthesis as well as an undersurface which is able to securely engage the natural patella. The artificial patella component further includes a tapered portion which is connected to the undersurface of the dome-shaped portion. The tapered portion of the artificial patella component includes at least two flexible lobes which are able to securely engage a cavity formed in the natural patella.

41 Claims, 2 Drawing Sheets

ARTIFICAL IMPLANT COMPONENT AND METHOD FOR SECURING SAME

This is a continuation of U.S. patent application Ser. No. 07/828,638, filed Jan. 31, 1992, now abandoned.

BACKGROUND OF THE INVENTION

This invention relates generally to a prosthetic total knee replacement system, and more specifically to an artificial patella component of a prosthetic total knee replacement system.

The hyaline anticular cartilage of the knee joint may undergo degenerative changes due to multiple etiologies. When these degenerative changes are advanced, irreversible and unresponsive to non operative management, it may ultimately become necessary to replace the natural knee joint with an artificial knee joint prosthetic system. On many of these occasions, it is necessary to surgically implant within the natural patella an artificial patella component which then articulates with the patella femoral groove of the femoral component of the total knee joint replacement system.

When such an artificial patella component is implanted, the anticular portions of the natural patella are initially surgically removed and the subchondral bone is cut by appropriate surgical instrumentation so as to form a "patella bed" into which the artificial patella component is securely implanted. When the artificial patella component is surgically implanted in its proper location in the natural patella, the articular surface of the artificial patella component is able to articulate with the patello femoral groove of the femoral component of the knee joint prosthesis in a manner similar to the way in which the natural patella would articulate with the femur of the natural knee. As one would expect, the means for securing the artificial patella component to the natural patella should be relatively strong in order to prevent loosening of artificial patella component from the natural patella during normal usage of the knee joint prosthesis.

Different methods are known in the art for securing an artificial patella component to the natural patella. In one of these methods, the natural patella is surgically altered so as to form two cylindrical cavities proximate to the center of the natural patella. The artificial patella component, which includes a flat undersurface and a cylindrical stem portion extending anteriorly from the undersurface, is secured to the natural patella by placing the stem portion of the artificial patella component into the smaller cylindrical cavity of the natural patella. The stem portion of the artificial patella component may also include a circumferential ridge which is able to cause mechanical interference with the sides of the cylindrical cavity of the natural patella so as to attach the artificial patella component to the natural patella more securely and at times without bone cement. Bone cement is usually applied to the contact area between the artificial patella component and the natural patella in order to further secure the artificial patella component to the natural patella. Some patella designs may have more than one solid small cylindrical peg in conjunction with an undersurface groove.

SUMMARY OF THE INVENTION

The present invention provides design features of an artificial patella component which ultimately provides rigid fixation to a natural patella when used in conjunction with an artificial knee joint prosthesis. The invention also encompasses the method of securing an artificial patella component to a natural patella as part of an artificial knee joint replacement system.

An advantage of the present invention is that an artificial patella component as described herein results in a more secure engagement between the artificial patella component and the natural patella.

Another advantage of the present invention is to provide an artificial patella component in which bone cement is able to attach more securely the artificial patella component to the natural patella, through means of macrointer digitation with a plurality of angled holes.

Yet another advantage of the present invention is to provide an artificial patella component which can be attached to a natural patella with relative ease.

A further advantage of the present invention is to provide an artificial patella component having a metal backing which can incorporate a modular threadable divergent hollow slit flexible peg.

The invention, in one form thereof, provides an artificial patella component which includes a tapered peg which is able to engage an undersized cavity which has been formed in the natural patella. The tapered peg of the artificial patella component includes two or more flexible lobes which diverge from each other in the anterior direction from the undersurface of the artificial patella component. The flexible lobes are compressible and thus engage the undersized cavity in the natural patella as the artificial patella component is clamped into position in the natural patella. Accordingly the flexible lobes of the artificial patella component are able to engage the undersized cavity of the natural patella in a press fit manner without permanent deformation so as to secure the artificial patella component to the natural patella.

The invention further provides, in one form thereof, a plurality of closed ended canals which are located on the undersurface of the dome-shaped portion of the artificial patella component. One set of these canals are angularly displaced from the antero-posterior centerline of the artificial patella component and to each other. The other set of canals are perpendicular to the undersurface. Accordingly, after bone cement is applied to the natural patella, the bone cement will become lodged in these undersurface canals of the artificial patella component as the artificial patella component engages the natural patella causing macro interdigitation so as to further secure the artificial patella component to the natural patella. These undersurface canals are effectively angled to each other Additional objects, advantages, and features of the present invention will become apparent from the following description and appended claims, taken in conjunction with the accompanying drawings.

DETAILED DESCRIPTION OF THE PREFERRED EMBODIMENTS

The following discussion of the preferred embodiments of the artificial patella component of the present invention is merely exemplary in nature and is not intended to limit the invention or its application or uses.

Figure 1:
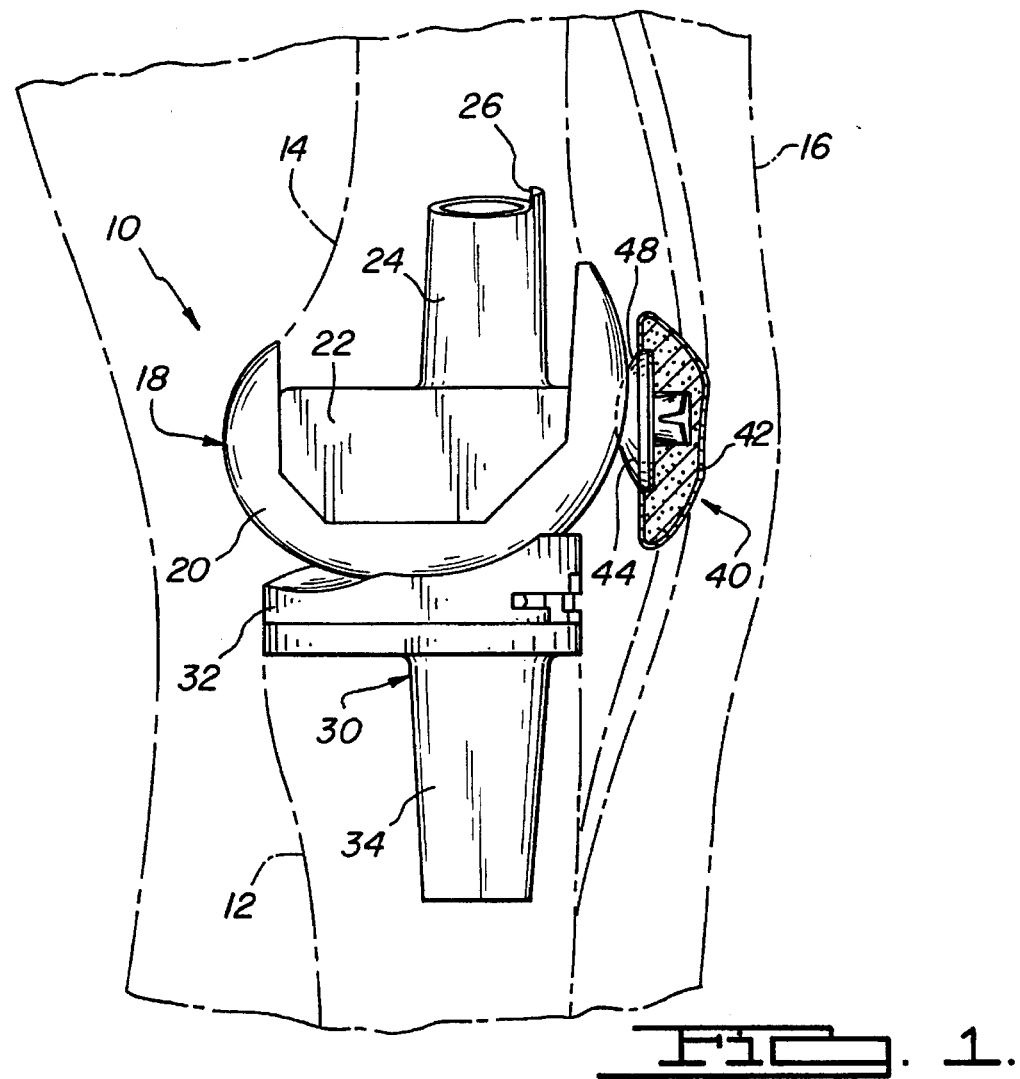
FIG. 1 is an illustration of a mid-longitudinal section of a human leg having an artificial knee joint prosthesis with an artificial patella component according to the first preferred embodiment of the present invention.

Referring to FIG. 1, there is shown a total knee joint prosthesis 10 depicted as being functionally secured to a tibia 12 and a femur 14 of a human leg 16. Knee joint prosthesis 10 includes a femoral component 18 which is rigidly connected to the distal end of the femur 14 after the femur 14 has been resected in a manner which is well known in the art. The femoral component 18 includes a condylar portion 20 which engages a tibial component which is more fully described below. Superiorly adjacent to the condylar portion 20 on the femoral component 18 is an intercondylar portion 22 is used to operatively engage a superiorly extending peg (not shown) on the tibial component so as to limit antero-posterior movement of the femoral component 18.

Connected superiorly to the intercondylar portion 22 of the femoral component 18 is a femoral stem boss 24. The femoral stem boss 24 is used to receive a support member (not shown) which is operable to secure the femoral component 18 to the femur 14. Positioned at a superior end of the femoral stem boss 24 is an anti-rotation member 26. The anti-rotation member 26 engages a recess in the support member so as to prevent rotation of the support member with respect to the femoral component 18. While the femoral component 18 is generally unitary in nature and is comprised of a biocompatible high strength alloy such as $Ti_4Al_6V$, other suitable materials may be used. Other distal femoral designs may also be used.

The knee joint prosthesis 10 further comprises a tibial component 30 having a tibial insert liner 32 which is able to articulate with the condylar portion 20 of the femoral component 18. The tibial component 30 is connected to the tibia 12 by an inferiorly extending tibial boss stem 34 which is able to receive a support member (not shown) which is secured to the tibia 12. The tibial component 30 is generally a unitary structure and is preferably formed from $Ti_4Al_6V$, while the tibial insert liner 32 is preferably made from ultra-high molecular weight polyethylene (UHMWP). However, other suitable materials and designs may be used.

The knee joint prosthesis 10 further comprises a patella 40 which includes a natural patella 42 and an artificial patella component 44. The artificial patella component 44 is attached to the natural patella 42 so as to provide an articulating surface between the patella 40 and the knee joint prosthesis 10. The artificial patella component 44 includes a dome-shaped portion 46 having an articular surface 48 shaped in a general spherical manner which is operable to articulate with the patello femoral groove (not shown) in the anterior condylar portion 20 of the femoral component 18. The spherical shape of the articular surface 48 of the artificial patella component 44 permits the patella 40 to remain relatively stationary as flexion of the knee joint prosthesis 10 occurs.

Figures 2, 3:
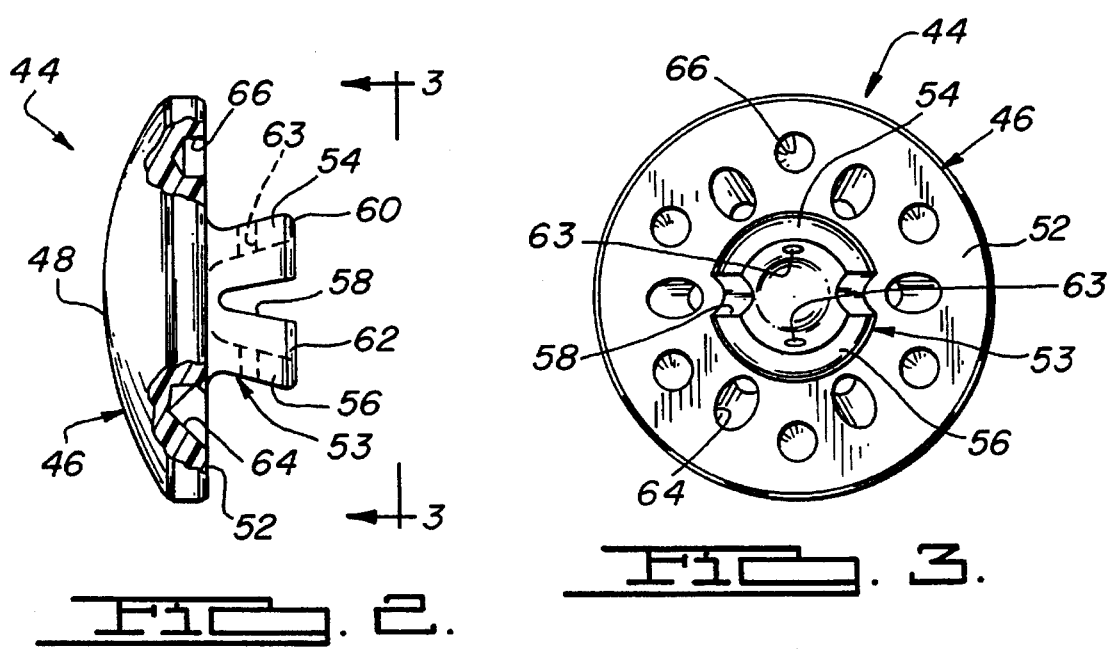
FIG. 2 is an enlarged cross-sectional longitudinal view of the artificial patella component.
FIG. 3 is an undersurface view of the artificial patella component taken along the line 3—3 in FIG. 2.

As shown in FIGS. 2 and 3, artificial patella component 44 further includes relatively flat undersurface 50. The undersurface 50 of the artificial patella component 44 is operable to engage a surgically prepared patella bed 52 formed in the natural patella 42 as discussed below. Extending anteriorly from the undersurface 50 of the artificial patella component 44 is a tapered peg 53 having two flexible divergent lobes 54 and 56 which are separated by a slot 58. "Tapered" is hereby considered to be in a direction toward the dome-shaped portion 46. The flexible lobes 54 and 56 are generally semicircular in shape and diverge from each other as they extend from the undersurface 50 of artificial patella component 44. Each of the flexible lobes 54 and 56 includes a lip portion 60 and 62 opposite the undersurface 50 which are used to facilitate engagement of the artificial patella component 44 with the natural patella 42 in the manner described below. In addition, each of the flexible divergent lobes 54 and 56 may have a centrally disposed transverse channel or cross hole 63. The channels 63 are used to receive bone cement when the artificial patella component 44 is attached to the natural patella 42 as more fully described below. In addition, the transverse hole 63 is used to screw in the modular threaded patella peg (FIG. 6) into the threaded undersurface of the patella.

Figure 6:
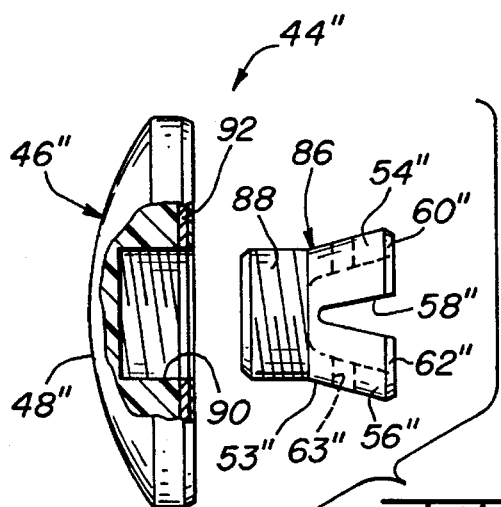
FIG. 6 is a longitudinal cross sectional view of yet another preferred embodiment of the present invention that is a modular threaded slit flexible peg with a transverse channel between the lobes, in a metal backed porous coated patella.

The artificial patella component 44 further comprises a first plurality of closed ended canals 64 and a second plurality of closed ended canals 66. The first and second plurality of canals 64 and 66 extend into the artificial patella component 44 from the undersurface 50 of the artificial patella component 44. The first plurality of canals 64 are oriented at an angle of approximately 45° from the antero-posterior centerline of the artificial patella component 44 and are generally directed toward the center of the dome of artificial patella component 44. The second plurality of canals 66 extend into the artificial patella component 44 in a direction perpendicular to the anterior surface 50 of the artificial patella component 44. The first plurality of canals 64 and the second plurality of canals 66 are oriented in an alternating configuration around the region of the undersurface 52 where the flexible divergent lobes 54 and 56 engage the undersurface 50. The first and second plurality of canals 64 and 66 improve the fixation between the natural patella 42 and the artificial patella component 44 as will be discussed in greater detail below. In a preferred embodiment, artificial patella component 44 is a unitary structure formed of UHMWP, though other suitable materials may be used. The patella implant can also be metal backed and coated with a porous surface for cementless fixation (FIG. 6).

Figure 4A:
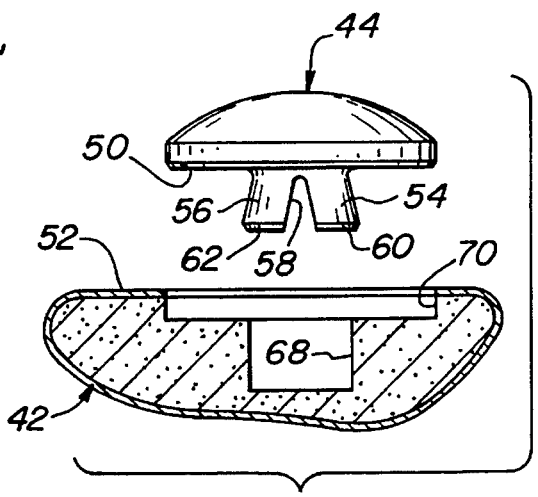
FIG. 4(A) is a partial cross-sectional view showing the artificial patella component and the surgically prepared natural patella of FIG. 1 prior to engagement.

The method of securing the artificial patella component 44 to the natural patella 42 will now be described with reference to FIGS. 4(A)–(C). The natural patella 42 is initially prepared to receive the artificial patella component 44 by reaming a first cavity 68 in the natural patella 42. The diameter of the first cavity 68 is such that it is slightly smaller than the largest distance separating the external surfaces of the flexible divergent lobes 54 and 56. In a preferred embodiment, the first cavity 68 is approximately 1 mm less than the greatest distance separating the external surfaces of the flexible divergent lobes 54 and 56. After the first cavity 68 has been reamed, a second larger cavity 70 is reamed concentric with the first cavity 68 such that the edge of the dome-shaped portion 46 of the artificial patella component 44 will seat inside of the natural patella 42. The formation of the patella bed 52 is completed after the first and second cavities 68 and 70 have been formed in the natural patella 42.

Figure 4B:
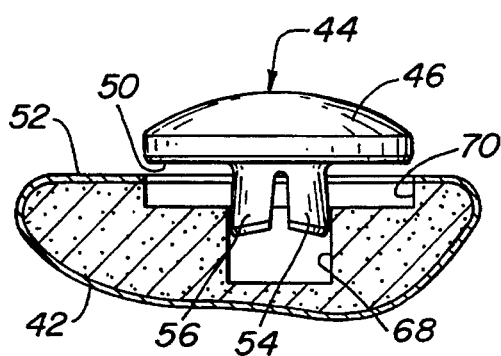
FIG. 4(B) is a partial cross-sectional view of the artificial patella component and the natural patella shown in FIG. 1 as the artificial patella component is being inserted into the surgically prepared natural patella.
Figure 4C:
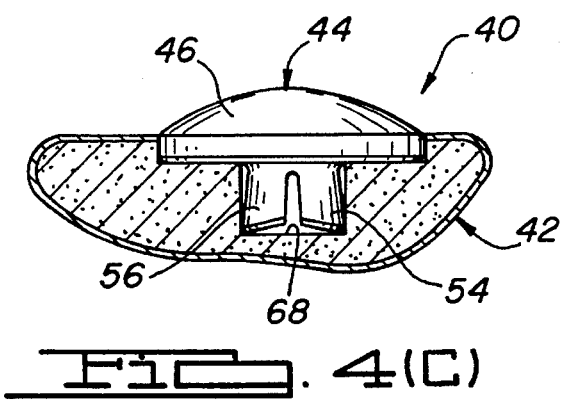
FIG. 4(C) is a partial cross-sectional view of the artificial patella component and the natural patella of FIG. 1 showing final engagement of the artificial patella component within the surgically prepared natural patella.

Turning to FIG. 4(B), the flexible divergent lobes 54 and 56 of the artificial patella component 44 are shown partially inserted in the first cavity 68. When the lips 60 and 62 of the flexible divergent lobes 54 and 56 engage the superior rim of the first cavity 68, the flexible divergent lobes 54 and 56 will be compressed inwardly so that the flexible divergent lobes 54 and 56 can be received into the first cavity 68. As the artificial patella component 44 is progressively inserted into the first cavity 68, the undersurface 50 of the artificial patella component 44 will eventually engage the bottom surface of the larger cavity 70 of the natural patella 42 as shown in FIG. 4(C). Since the flexible divergent lobes 54 and 56 remain in a flexed configuration, they will be continually applying a force by virtue of design and material characteristics against the walls of the first cavity 68 and secure the artificial patella component 44 to the natural patella 42, in a press fit manner.

The press fit engagement between flexible divergent lobes 54 and 56 and the cavity 68 provides only part of the possible attachment mechanism of the artificial patella component 44. Bone cement (not shown) may also be applied to both of the first and second cavities 68 and 70 as well as patella bed 52 prior to engagement between the artificial patella component 44 and the natural patella 42. Consequently, not only is the artificial patella component 44 secured in a press fit manner to the natural patella 42, but the artificial patella component 44 is also cemented to the natural patella 42. It is stressed, however, that this design is able to provide a sufficient attachment between the artificial patella component 44 and the natural patella 42 without the need of bone cement, although cemented fixation is generally used more than cementless fixation with non-metal backed patellae.

As will be appreciated by those skilled in the art, the first and second cavities 68 and 70 provide a recessed or inlaid area into which the artificial patella component 44 can be cemented to the natural patella 42 or from which bone ingrowth may occur. Furthermore, the slot 58 provides a canal for accepting bone cement to provide additional fixation. In addition, bone cement will also flow into the first and second plurality of canals 64 and 66 as discussed above, thereby further increasing the surface area upon which the bone cement may act. As will be appreciated by those skilled in the art, the macro interdigitation associated with the first and second plurality of canals 64 and 66 provides a greater degree of security against loosening of the artificial patella component 44 as compared to other designs. The bone cement in the first and second plurality of angled holes 64 and 66 finally locks the patella compound 44 onto the patella bed 52. If the non-metal backed patella component 44 is implanted in a cementless fashion, then the plurality of canals 64 and 66 and slot 58 can be filled with cancellous bone acting as bone graft to enhance boney ingrowth and bone graft incorporation eventually.

Figure 5:
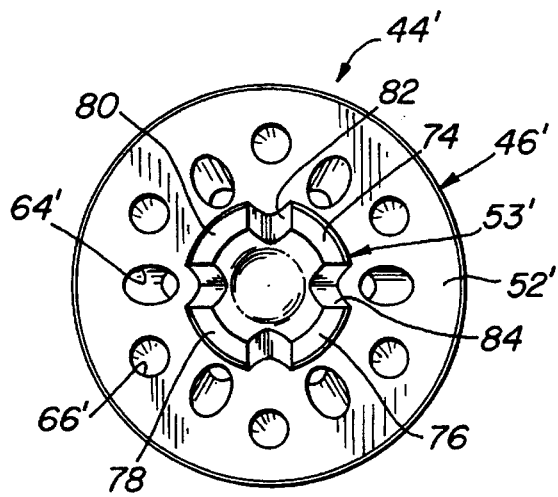
FIG. 5 is an undersurface view of an artificial patella component according to the second preferred embodiment of the present invention that is with the divergent flexible peg having four lobes.

Now turning to FIG. 5, a second preferred embodiment of the artificial patella component 44' is shown. Each of the primed reference numerals correspond exactly to the unprimed reference numerals of FIG. 3 except as indicated. The preferred embodiment of FIG. 5 comprises four flexible divergent lobes 74–80 instead of the two flexible divergent lobes 54 and 56 of the first embodiment. The flexible divergent lobes 74–80 are about one half the arcuate size of the flexible divergent lobes 54 and 56 of the first embodiment and provide for four independent areas of engagement between the artificial patella component 44' and the first cavity 68' of the natural patella 42'. In addition, the slots 82 and 84 formed by the flexible divergent lobes 74–80 provides greater area for accepting bone cement to enable a more rigid fixation of the artificial patella component 44' to the natural patella 42'.

Now turning to FIG. 6, yet another preferred embodiment is shown as a longitudinal cross-sectional view of an artificial patella component 44" similar to that of FIG. 3. Each of the double primed reference numerals correspond exactly to the unprimed reference numerals of FIG. 3, except where indicated. The artificial patella component 44" is shown as having the same geometric configuration as the artificial patella component 44 of FIG. 2, but in which the flexible divergent lobes 54" and 56" are part of a modular threadable member 86". The threadable member 86" has a stem 88" for threadable engagement within a threaded cavity 90" located in the dome-shaped portion 46". This embodiment may be preferred when the dome-shaped portion 46" includes a porous metal backing 92 secured to the undersurface 52" of the artificial component 44". In this manner, the flexible divergent lobes 54" and 56" can be rigidly secured to the dome-shaped portion 46" despite the presence of the metal backing 92. As will be appreciated by those skilled in the art, the metal backing 92 may be porous coated to facilitate bone ingrowth so as to provide additional stability.

The foregoing discussion discloses and describes merely exemplary embodiments of the present invention. As those skilled in the art will appreciate, the present invention may be used with resurfacing patellae as well as inlaid or recessed patellae. One skilled in the art will readily recognize from such discussion, and from the accompanying drawings and claims, that various changes, modifications and variations can be made therein without departing from the spirit and scope of the invention as defined in the following claims.

What is claimed is:

1. An artificial patella component of a knee joint prosthesis, the knee joint prosthesis having a femoral component, said artificial patella component adapted to be secured to a natural patella having a cavity, said artificial patella component comprising:

a dome-shaped portion having a spherical articular surface operable to articulate said knee joint prosthesis and an undersurface operable to engage said natural patella; and a tapered portion connected to said undersurface of said dome-shaped portion, said tapered portion including a plurality of flexible lobes being operable to engage said cavity in said natural patella.

2. The artificial patella component according to claim 1, wherein said plurality of flexible lobes are substantially semicircular in cross-section and diverge from each other as said flexible lobes extend from said dome-shaped portion.

3. The artificial patella component according to claim 1, wherein said dome-shaped portion includes a threaded cavity extending from said undersurface in a direction toward said spherical articular surface said artificial patella component further comprising a threaded member being attached to said plurality of flexible lobes and being able to threadably engage said threaded cavity.

4. The artificial patella component according to claim 3, further including a metal backing disposed on said undersurface, said threaded member being operable to engage said dome-shaped portion through the metal backing.

5. The artificial patella component according to claim 1, wherein said plurality of flexible lobes include four flexible lobes which diverge from each other as said four flexible lobes extend from said undersurface, said four flexible lobes being operable to flex towards each other upon engagement with said cavity of said natural patella.

6. The artificial patella component according to claim 1, further comprising a first plurality of canals disposed in said dome-shaped portion of said artificial patella component, said first plurality of canals extending from said undersurface of said dome-shaped portion.

7. The artificial patella component according to claim 6, wherein said dome-shaped portion includes a centerline perpendicularly disposed with respect to said undersurface of said dome-shaped portion, said first plurality of canals being angularly displaced with respect to said centerline.

8. The artificial patella component according to claim 7, further comprising a second plurality of canals extending from said undersurface of said dome-shaped portion, said second plurality of canals being disposed perpendicularly with respect to said undersurface.

9. The artificial patella component according to claim 8, wherein at least one of said first plurality of canals is disposed adjacent to one of said second plurality of canals.

10. The artificial patella component according to claim 1, wherein at least one of said flexible lobes includes a transverse channel extending substantially parallel to said undersurface of said artificial patella component.

11. A method of securing an artificial patella component to a natural patella, said method comprising the steps of:
providing an artificial patella component including a dome-shaped portion having a spherical articular surface and a substantially flat undersurface, said artificial patella component further including a plurality of flexible lobes extending from the undersurface;
surgically preparing a natural patella for receiving said artificial patella component including forming a cavity in said natural patella; and
inserting said plurality of flexible lobes into said cavity such that said flexible lobes are compressed together as they are being inserted into said cavity thereby securing said artificial patella component to said natural patella.

12. The method according to claim 11, wherein said artificial patella component comprises a threaded member which is operable to threadably engage said dome-shaped portion of said artificial patella component, said threaded member being operable to carry said plurality of flexible lobes, said method comprising the additional step of threadably engaging said threaded member of said artificial patella component with said dome-shaped portion of said artificial patella component.

13. The method according to claim 11, wherein said step of providing an artificial patella component includes the step of providing a first plurality of canals extending from said undersurface of said artificial patella component.

14. The method according to claim 13, wherein said dome-shaped portion includes a centerline perpendicularly disposed with respect to said undersurface of said artificial patella, said step of providing a first plurality of canals includes the step of providing at least one canal which is angularly offset from said centerline.

15. The method according to claim 14, wherein said step of providing an artificial patella component further includes the additional step of providing a second plurality of canals which extend substantially perpendicular from said undersurface of artificial patella component in a direction toward said spherical articular surface of said artificial patella component.

16. The method according to claim 15, further comprising the additional step of allowing bone cement disposed between said undersurface of the artificial patella component and said natural patella to flow into said first and second plurality of canals.

17. The method according to claim 11, wherein said step of providing said artificial patella component includes the step of forming a transverse channel in at least one of said flexible lobes.

18. An artificial patella component of a knee joint prosthesis, said knee joint prosthesis having a femoral component, said artificial patella component adapted to be secured to a natural patella having a cavity, said artificial patella component comprising:
a dome-shaped portion including a spherical articular surface operable to articulate with said knee joint prosthesis and an undersurface operable to engage said natural patella, said dome-shaped portion having a centerline perpendicularly disposed with respect to said undersurface of said dome-shaped portion;
a tapered portion extending from said undersurface of said dome-shaped portion, said tapered portion being operable to engage a cavity formed in said natural patella, said tapered portion includes a plurality of flexible lobes extending from said undersurface of said dome-shaped portion; and
a plurality of canals extending from said undersurface of said dome-shaped portion, said plurality of canals including at least one canal disposed perpendicularly with respect to said undersurface of said dome-shaped portion and at least one canal angularly displaced from said centerline of said dome-shaped portion.

19. An artificial implant component operable to articulate with a portion of a joint prosthesis, said artificial implant component adapted to be secured to a portion of the human body having a cavity, said artificial implant component comprising:
an articulating portion operable to articulate with a portion of said joint prosthesis; and
a tapered portion extending from said articulating portion, said tapered portion including a plurality of flexible lobes being operable to engage said cavity in said portion of said human body.

20. The artificial implant component according to claim 19, wherein said plurality of flexible lobes are substantially semicircular in cross-section and diverge from each other as said flexible lobes extend from said articulating portion.

21. The artificial implant component according to claim 19, wherein said articulating portion includes an internally threaded cavity, said tapered portion further including a threaded member being operable to carry said plurality of flexible lobes and being able to threadably engage said internally threaded cavity of said articulating portion.

22. The artificial patella component according to claim 21, further including a metal backing disposed between said articulating portion and said tapered portion, said tapered portion being operable to engage said articulating portion through the metal backing.

23. The artificial implant component according to claim 19, wherein said plurality of flexible lobes include four flexible lobes which diverge from each other as said four flexible lobes extend from said articulating portion, said four flexible lobes being operable to flex towards each other upon engagement with said cavity of said natural component.

24. The artificial implant component according to claim 19, further comprising a first plurality of canals disposed in said articulating portion of said artificial implant component.

25. The artificial implant component according to claim 24, wherein said articulating portion includes a generally planar surface through which said first plurality of canals extend, said first plurality of canals being angularly offset with respect to the normal of said surface.

26. The artificial implant component according to claim 25, further comprising a second plurality of canals disposed in said articulating portion of said artificial implant component, said second plurality of canals being angularly displaced with respect to said first plurality of canals.

27. The artificial implant component according to claim 26, wherein at least one of said first plurality of canals is disposed between two of said second plurality of canals.

28. The artificial implant component according to claim 19, wherein at least one of said flexible lobes includes a transverse channel.

29. A method of securing an artificial implant component having an articulating surface to a portion of the human body, said method comprising the steps of:

providing an artificial implant component having a first portion mechanically communicating with a second portion, said first portion having said articulating surface and said second portion including a plurality of flexible lobes;

surgically preparing said portion of said human body for receiving said artificial implant component including forming a cavity in said portion of said human body; and inserting said plurality of flexible lobes into said cavity such that said flexible lobes are compressed together as they are being inserted into said cavity thereby securing said artificial implant component to said portion of said human body.

30. The method according to claim 29, wherein said second portion further includes a threaded member which is operable to threadably engage said first portion of said artificial implant component, said threaded member being operable to carry said plurality of flexible lobes, said method comprising the additional step of threadably engaging said threaded member with said first portion of said artificial implant component.

31. The method according to claim 29, wherein said step of providing an artificial implant component includes the step of providing a first plurality of canals extending in a first direction in said first portion of said artificial implant component.

32. The method according to claim 31, wherein said first portion of said artificial implant component includes a generally planar surface, said step of providing a first plurality of canals includes the step of providing at least one canal which is angularly offset with respect to the normal of said planar surface of said artificial implant component.

33. The method according to claim 32, wherein said step of providing an artificial implant component further includes the additional step of providing a second plurality of canals which are angularly offset with respect to said first plurality of canals.

34. The method according to claim 33, further comprising the additional step of allowing bone cement to flow into said first and second plurality of canals as said plurality of flexible lobes are inserted into said cavity.

35. The method according to claim 33, further comprising the additional step of allowing bone graft to be placed into said first and second plurality of canals as said plurality of flexible lobes are inserted into said cavity.

36. The method according to claim 33, further comprising the additional step of allowing bone graft to be disposed between said flexible lobes.

37. The method according to claim 29, wherein said step of providing said artificial implant component includes the step of forming a transverse channel in at least one of said flexible lobes.

38. An artificial implant component operable to movably articulate with a portion of a joint prosthesis, said artificial implant component adapted to be secured to a portion of the human body having a cavity using bone cement, said artificial implant component comprising:

an articulating portion operable to engage a portion of said joint prosthesis, said articulating portion having an axial centerline; and a plurality of canals partially disposed in said articulating portion of said, artificial implant component, said plurality of canals including at least one canal disposed parallel to said axial centerline of said articulating portion and at least one canal angularly displaced from the said axial centerline of said articulating portion, whereby said canals are operable to receive bone cement when said artificial implant component is secured to the portion of the human body using bone cement.

39. The artificial implant component according to claim 38 further comprising a tapered portion extending from said articulating portion, said tapered portion being operable to engage said cavity in said portion of said human body.

40. The artificial implant component of claim 39, wherein said tapered portion includes a plurality of flexible lobes being operable to engage said cavity formed in said portion of said human body.

41. An artificial implant component operable to articulate with a portion of a joint prosthesis, said artificial implant component being secured to a portion of the human body having a cavity, said artificial implant component comprising:

an articulating portion operable to engage a portion of said joint prosthesis; and a hollow peg extending from said articulating portion and being operable to be inserted into said cavity of said portion of said human body, .said hollow peg forming a plurality of flexible lobes.

* * * * *

UNITED STATES PATENT AND TRADEMARK OFFICE
CERTIFICATE OF CORRECTION

PATENT NO. : 5,480,443
DATED : January 2, 19966
INVENTOR(S) : Elias

It is certified that error appears in the above-identified patent and that said Letters Patent is hereby corrected as shown below:

ON THE TITLE PAGE, under OTHER PUBLICATIONS, second column, sixth document listed, "Advetising" should be --Advertising--.

Column 3, line 46, "Ti$_4$A1$_6$V" should be --Ti-4Al-6V--.

Column 3, line 55, "Ti$_4$A1$_6$V" should be --Ti-4Al-6V--.

Column 10, line 52, claim 41, after "," delete ".".

Signed and Sealed this

Thirtieth Day of June, 1998

Attest:

BRUCE LEHMAN

Attesting Officer     Commissioner of Patents and Trademarks